United States Patent [19]

Schutt

[11] 4,260,684

[45] Apr. 7, 1981

[54] STEREOSELECTIVE RESOLUTION OF PHENYLGLYCINE DERIVATIVES AND 4-HYDROXYPHENYLGLYCINE DERIVATIVES WITH ENZYME RESINS

[75] Inventor: Hermann Schutt, Wuppertal, Fed. Rep. of Germany

[73] Assignee: Bayer Aktiengesellschaft, Leverkusen, Fed. Rep. of Germany

[21] Appl. No.: 8,631

[22] Filed: Feb. 1, 1979

[30] Foreign Application Priority Data

Feb. 21, 1978 [DE] Fed. Rep. of Germany ....... 2807286

[51] Int. Cl.³ .................... C12P 13/04; C07B 19/02; C12P 13/02
[52] U.S. Cl. .................... 435/106; 435/128; 435/129; 435/280; 560/37; 560/39; 560/41; 560/251; 562/401; 564/155
[58] Field of Search .................... 260/562 R, 562 N; 195/2, 29, 30; 562/443, 444, 450, 401; 560/37, 39, 41; 435/106, 128, 129, 135, 136, 174, 180, 280

[56] References Cited

U.S. PATENT DOCUMENTS

| | | | |
|---|---|---|---|
| 3,832,388 | 8/1974 | Lorenz | 562/401 X |
| 3,929,574 | 12/1975 | Wood et al. | 195/29 |
| 3,963,573 | 6/1976 | Stauffer | 195/29 |
| 3,971,700 | 7/1976 | Boesten | 195/29 |
| 4,033,817 | 7/1977 | Gregor | 195/2 |
| 4,080,259 | 3/1978 | Boesten et al. | 195/2 |
| 4,092,219 | 5/1978 | Lin et al. | 195/29 |
| 4,108,723 | 8/1978 | Hirohara et al. | 195/2 |
| 4,132,596 | 1/1979 | Meiller et al. | 195/63 |

*Primary Examiner*—Natalie Trousof
*Assistant Examiner*—Vera C. Clarke
*Attorney, Agent, or Firm*—Sprung, Felfe, Horn, Lynch & Kramer

[57] ABSTRACT

The invention encompasses a process for the stereoselective resolution of DL-phenylglycine derivatives using proteolytic enzymes bonded to resin carriers.

14 Claims, No Drawings

STEREOSELECTIVE RESOLUTION OF PHENYLGLYCINE DERIVATIVES AND 4-HYDROXYPHENYLGLYCINE DERIVATIVES WITH ENZYME RESINS

The invention relates to a new enzymatic process for the stereoselective resolution of a DL-phenylglycine derivative comprising hydrolysing an ester or amide group on an N-acyl-L-phenylglycine ester or amide in an N-acyl-DL-phenyl-glycine ester or amide in solution by the action of an enzyme bonded to a carrier, separating the N-acyl-D-phenylglycine ester or amide from the N-acyl-L-phenylglycine and then, if desired, hydrolysing under acid conditions, the ester or amide group of the D-enantiomer and the acyl group.

D-Phenylglycine and D-4-hydroxyphenylglycine are used as starting substances for the preparation of semi-synthetic antibiotics of the penicillin series. L-Phenylglycine is a starting substance for L-aspartyl-L-phenylglycine methyl ester, which is used as a sweetener.

The method introduced in industry for the resolution of the racemate of DL-phenylglycine and of DL-4-hydroxyphenylglycine is fractional crystallisation of the salts of the two aminoacids using DL-camphorsulphonic acid (J.P. Greenstein and M. Winitz, Chemistry of Aminoacids, Volume 1 (1961) 658). Because of the high price of camphorsulphonic acid, this compound must be recovered as completely as possible, which can scarcely be realised industrially. There has therefore been no lack of attempts to carry out resolution of racemates of derivatives of phenylglycine and of 4-hydroxyphenylglycine on a completely different basis to fractional crystallisation of diastereoisomeric compounds. More recent processes attempt to utilise the high stereospecificity of certain enzymes. However, a number of disadvantages must be accepted in the case of the processes hitherto disclosed.

In DE-OS (German Published Specification) No. 2,526,594, L-phenylglycine amide in DL-phenylglycine amide is hydrolysed to L-phenylglycine by an aminopeptidase suitable for this purpose and the L-phenylglycine is separated off from the unchanged D-phenylglycine amide, the enzyme leucine aminopeptidase (EC 3.4.1.1.) used being partly bonded to a carrier. This process can only be carried out in a very dilute mixture because the hydrolysis product L-phenylglycine would, as a result of being sparingly soluble, crystallise on the enzyme or enzyme resin and thus cause it to stop acting in a very short time. This results in large volumes of mixture which must be concentrated, with the expenditure of energy, in order to isolate the desired product. Corresponding statements apply to the processes of DE-OS (German Published Specification) No. 2,621,076 and British Pat. No. 1,369,462, in which L-phenylglycine and L-4-hydroxyphenylglycine are formed from phenyl- or 4-hydroxyphenylhydantoins or from N-phenacetyl-DL-4-hydroxyphenylglycine.

It is also known, from Biochem. J. (1972), 126, 645–657, to resolve DL-2-acetamido-2-phenylacetic acid methyl ester into D-2-acetamido-2-phenylacetic acid methyl ester and L-2-acetamido-2-phenylacetic acid with carrier-free α-chymotrypsin, only 60% and 52.5%, respectively, of theory of the products being obtained.

It has now been found, surprisingly, that the enzymatic resolution of phenylglycine derivatives can be carried out at a substantially higher concentration when N-acyl-DL-phenylglycine esters or amides, as the starting material, are subjected to enzymatic hydrolysis, in solution, on enzymes bonded to carriers.

The compounds to be resolved correspond, preferably to the general formula

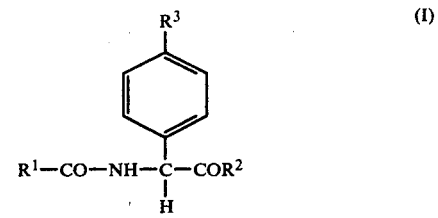

DL-Form in which
R$^1$ denotes a hydrogen atom or a radical of an optionally substituted aliphatic or araliphatic monocarboxylic or dicarboxylic acid or of a naturally occurring or synthetic α-aminocarboxylic acid,
R$^2$ denotes an alkoxy group, an amino group which is optionally monosubstituted or disubstituted by alkyl, or a radical of a naturally occurring or synthetic α-amino-acid and
R$^3$ denotes a hydrogen atom or a hydroxyl, alkoxy, aralkoxy, aryloxy, cycloalkoxy or acyloxy group.

Optionally substituted aliphatic radicals R$_1$ are, above all, C$_1$-C$_9$-alkyl or alkenyl groups which are optionally substituted by halogen, in particular fluorine or chlorine, preferably C$_1$-C$_4$-alkyl or alkenyl groups which are optionally monosubstituted to trisubstituted by fluorine or chlorine; araliphatic radicals R$_1$ are, in particular, phenyl-C$_1$-C$_2$-alkyl groups, preferably the benzyl radical; and the radicals R$_1$ and R$_2$ which are derived from α-amino-acid are, in particular, those derived from naturally occurring α-amino-acids. Alkoxy groups R$_2$ are, in particular, C$_1$-C$_4$-alkoxy, preferably methoxy and ethoxy. Amino groups which areoptionally monosubstituted or disubstituted by alkyl are, preferably, amino, methylamino, ethylamino, dimethylamino and diethylamino. Alkoxy R$_3$ is, in particular, C$_1$-C$_4$-alkoxy; aralkoxy R$_3$ is, in particular, benzyloxy, aryloxy R$_3$ is, in particular, phenyloxy; cycloalkoxy R$_3$ is, in particular, C$_5$ and C$_6$-cycloalkoxy; and acyloxy R$_3$ is, in particular, C$_1$-C$_4$-alkylcarbonyloxy which is optionally substituted by 1 to 3 fluorine or chlorine atoms.

Preferred compounds of the formula I are, on the one hand, those in which R$_1$ denotes hydrogen, mono-, di- or tri-chloromethyl, trifluoromethyl or ω-carboxy-C$_2$-C$_6$-alkyl, R$_2$ denotes methoxy or ethoxy and R$_3$ denotes hydrogen, and, on the other hand, those in which R$_1$ denotes hydrogen, methyl, mono-, di- or tri-chloromethyl, trifluoromethyl or ω-carboxy-C$_2$-C$_6$-alkyl, R$_2$ denotes methoxy or ethoxy and R$_3$ denotes hydroxyl, methoxy, ethoxy or acetoxy.

Possible solvents for the N-acyl-DL-phenylglycine esters and amides are anhydrous or water-containing organic solvents, in particular water-miscible solvents, for example dioxane, ethanol and acetonitrile.

Possible enzymes are, in particular, proteolytic enzymes, preferably serine proteases and sulphydryl-proteases, preferably subtilisin (EC 3.4.4.16.), α-chymotrypsin (EC 3.4.4.5.), papain (EC 3.4.4.10.), ficin or bromelain, the first two enzymes having a serine radical in the active centre of the aminoacid chain whilst the latter enzymes contain cysteine, as the active centre, in the aminoacid chain. Subtilisin is preferred.

About 100 mg to 1 g of enzyme bonded to a carrier are preferably employed per mol of compound to be resolved, and this enzyme can be re-used at least twenty times, whilst, in the process of Biochem. J., considerably larger amounts of enzyme must be used which, as a dissolved product, can be recovered only with difficulty and in small proportions.

Proteolytic enzymes which are isolated from *Bacillus subtilis* and *Bacillus licheniformis* and which are added to washing agents to remove protein residues are particularly suitable. These industrial enzymes are known chiefly by the trade names "Maxatase" (manufacturer: Gist-Broacdes N.V., Delft/Holland), "Optimase" (manufacturer: Miles-Kali-Chemie, Hanover) and "Alcalase" (manufacturer: Novo Industrie AS, Copenhagen/Denmark).

The properties of the proteolytic enzymes, in particular their biochemical actions, are described in the following literature: G. E. Perlmann and L. Lorand, Methods in Enzymology, 19 (1970) 199 to 215; P. Desnuelle, The Enzymes, 4 (1960) 93 and G. E. Perlmann and L. Lorand, Methods in Enzymology, 19 (1970) 226 to 244.

The proteolytic enzymes can be coupled to the polymeric carrier by a covalent bond, via a lysine radical which is not essential for the catalysis. Adsorption of the enzyme onto the pores of a charged carrier and subsequent cross-linking with glutarodialdehyde is also possible.

Possible enzyme carriers are polymeric, porous carriers, such as cellulose, dextran, starch, polyacrylamide gels, "Sepharose" (Trade Mark), "Sephadex" (Trade Mark) or various organic copolymers of acrylamide, methacrylates or methacrylamide and maleic anhydride, according to DE-OS (German Published Specifications) Nos. 2,215,539 and 2,215,687. Membranes of cellulose esters, cellulose acetate or polyamides, through which the substrate solution flows continuously, can also be used as enzyme carriers (D. J. Imnan and W. E. Hornby, Biochem. J., 129 (1972) 255 to 262).

Polymeric acrylic acid esters, such as Amberlite XAD-7 and XAD-8, and the weakly acid cation exchanger IRC 50 (Rohm and Haas, USA) have proved particularly favourable for the adsorption of the proteolytic enzymes.

After crosslinking the adsorbed enyzmes with 0.5–2.5% of glutardialdehyde, a very active enzyme resin with a very long life can be prepared.

Particularly preferred carriers are a copolymer of a methacrylate, methacrylic acid and maleic anhydride, optionally crosslinked by glutardialdehyde, and, especially in the case of substilisin, α-chymotrypsin, papain, ficin and bromelain, a copolymer of tetraethylene glycol dimethacrylate, methacrylic acid and maleic anhydric, optionally crosslinked by glutardialdehyde.

The enzymes are coupled to the porous, insoluble carriers by methods which are in themselves known. For coupling to the polymeric carrier, the enzyme is reacted under conditions which are optimum for the stability of the enzyme. The effectiveness of the coupling can be determined by measuring the enzymatic activity on the polymer and in the wash water. When used in a batch process, the polymeric enzyme can easily be separated off from the reaction solution by sedimentation or filtration and can be employed several times. The enzyme carrier can also be filled into columns and the substrate solution can flow through it in this form.

The N-acyl esters and amides, employed in the process according to the invention, of the phenylglycines are obtained by acylating the corresponding aminoacid ester hydrochlorides or amide hydrochlorides respectively with stoichiometric amounts of an acid anhydride, such as acetic anhydride, and then separating off the N-acyl derivative from the aqueous phase with organic solvents, such as chloroform or methylene chloride.

Industrial processes using enzymes bonded to carriers are particularly economical if the processes can be carried out at high concentrations of substrate. In a high concentration in aqueous dioxane, ethanol or acetonitrile, the N-acyl esters and amides of phenylglycines are in the form of clear solutions. It is possible to obtain a 10% strength solution of N-acetyl-DL-phenylglycine methyl ester in a dioxane/water mixture (1:3, by volume). Further N-acetyl ester can be dissolved by increasing the proportion of organic solvent. At high concentrations, the solvents mentioned act as precipitating agents for proteins. This disadvantage is not present in the case of the use, according to the invention, of enzymes bonded to carriers, since in these enzymes, the spatial fixing arrangement greatly prevents interaction of the enzyme molecules with one another, so that aggregation of the enzyme molecules leading to precipitation does not take place (K. Tamizawa and M. L. Bender, J. Biol. Chem., 249 (1974) 2130 to 2134).

Enzymatic resolution of the N-acyl-DL-phenylglycine esters is preferably carried out at a temperature of 20° to 40° C. in a pH range of 6 to 8, the pH value preferably being kept constant at 7.8 by adding a strong base. The substrate is stable under the reaction conditions. The course and the end point of the enzymatic reaction can be determined by neutralisation of the H+ ions formed. Neutralisation can be effected by inorganic bases as well as by organic bases.

After the enzymatic reaction has ended, the products, that is to say the N-acyl D-ester or the N-acyl D-amide and the N-acyl L-acid of the phenylglycines, are extracted from the aqueous reaction medium by shaking or stirring with organic solvents. The D-esters or D-amides are separated from the L-acids in the customary manner by rendering the reaction solution alkaline and extracting the esters or amides with an organic solvent, such as chloroform, ethyl acetate, methylene chloride or butyl acetate. The aqueous phase which remains is then rendered acid, for example with sulphuric acid, and again extracted with ethyl acetate. The optical purity of the resulting compounds is then investigated.

In order to prepare D- and L-phenylglycin, the two compounds are heated at 80° C. in 2 N hydrochloric acid for 4 hours. After cooling the solution, it is adjusted to pH 6 with sodium hydroxide solution or aqueous ammonia and cooled to 4° C. The phenylglycine which has crystallised out is filtered off and dried and its optical purity is investigated.

It has already been disclosed that microbial and animal serine proteases, such as Carlsberg and Novo subtilisins or chymotrypsin can resolve some N-acyl-L-aminoacid esters (A. O. Barel and A. N. Glazer, J. Biol. Chem., 243 (1968) 1344 to 1348 and U.S. Pat. No. 3,963,573).

However, these esters are considerably different from the derivatives of phenylglycine which are to be resolved according to the invention.

According to Chemical Reviews 46 (1950), pages 69 to 153, in particular 119 to 122, similar results with acylated phenylglycine esters could not be expected.

The following examples are illustrative but not limitative of the various aspects of the invention.

EXAMPLE 1

Preparation of N-acetyl-DL-phenylglycine methyl ester 41.4 g (0.205 mol) of DL-phenylglycine methyl ester hydrochloride are dissolved in 200 ml of water. The solution is cooled to 4° C. and adjusted to pH 6 to 7 with a saturated $NaHCO_3$ solution. 25 ml (0.26 mol) of acetic anhydride are slowly added dropwise, whilst stirring, and the pH value is kept between 6 and 7 by simultaneously adding the $NaHCO_3$ solution. A white precipitate is formed. The suspension is made up to 1.5 l with water and extracted by stirring with 1 l of chloroform or methylene chloride in portions. The combined chloroform phases are dried over $Na_2SO_4$ and filtered and the filtrate is concentrated as much as possible with the aid of a rotary evaporator. The N-acyl ester which has precipitated is dried in vacuo over $P_2O_5$ and paraffin. 36.0 g (84.7% of theory) of melting point 79° to 80° C. are obtained.

Thin layer chromatography on silica gel plates in the solvent system n-butanol/$CH_3COOH$/$H_2O$=4/1/1 gave a zone, which could be stained with iodine, with a $R_f$ value of 0.59 to 0.61. The compound prepared did not react with ninhydrin. The NMR spectrum corresponded to the formula.

EXAMPLE 2

Preparation of N-acetyl-DL-phenylglycine ethyl ester 75.6 g of N-acetyl-DL-phenylglycine ethyl ester (67.3% of theory) of melting point 63° C. were obtained from 112.4 g (0.52 mol) of DL-α-phenylglycine ethyl ester. HCl as described in Example 1.

The compound does not react with ninhydrin and is a single compound in the thin layer chromatogram ($R_f$ value=0.61), after staining with iodine. The NMR spectrum corresponds to the formula.

EXAMPLE 3

Preparation of N-acetyl-DL-4-hydroxyphenylglycine methyl ester 25 g (0.115 mol) of DL-4-hydroxyphenylglycine methyl ester hydrochloride were reacted as described in Example 1 to give 12.8 g of N-acetyl-DL-4-hydroxyphenylglycine methyl ester (50.1% of theory) of melting point 112° to 115° C.

By means of thin layer chromatography in the solvent system of Example 1, in addition to a zone which can be stained only with iodine ($R_f$ value=0.59 to 0.61), a trace of a further zone which reacts with ninhydrin and iodine can be detected ($R_f$ value=0.31). This zone corresponds to a small proportion of unreacted DL-4-hydroxyphenylglycine methyl ester.

EXAMPLE 4

Preparation of a subtilisin/anhydride resin 30 g of an anhydride resin (composition: 80% by weight of tetraethylene glycol dimethacrylate, 10% by weight of methacrylic acid and 10% by weight of maleic anhydride), washed with acetone, are suspended in 400 ml of water, and 40 ml of aqueous triethylamine solution are added. The pH value is adjusted to 6.2 with 0.1 M acetic acid, and 1 g of subtilisin (Alcalase Novo, 6.59 Anson units/g, manufacturer: Novo AS, Copenhagen/Denmark) is added, whilst stirring. The pH value is kept at 6.2 by titration with 1 N NaOH. After 12 hours, the enzyme resin is filtered off and washed on the filter several times with 0.05 M phosphate buffer +1 NaCl, of pH 7.5, and 0.5 M phosphate buffer of pH 7.5. Of the activity of 53,000 ATEE units originally employed, 21,400 ATEE (N-acetyl-L-tyrosine ethyl ester) units (40.4%) can be detected in the filtrate and 6,466 ATEE units (12.2%) are covalently bonded to the enzyme resin.

EXAMPLE 5

Preparation of a subtilisin/anhydride resin (crosslinked with glutarodialdehyde)

9 g of the moist anhydride resin from Example 4 are suspended in 90 ml of water and the pH is adjusted to 5.7. 1.35 g of subtilisin (Alcalase Novo, 6.59 Anson units/g, manufacturer: Novo AS, Copenhagen/Denmark) are added, whilst stirring. The resin is kept at pH 5.7 with 0.1 N NaOH for 12 hours and then filtered off. 50 ml of a 0.625% strength glutardialdehyde solution are added, whilst stirring, and after a reaction time of 3 hours at room temperature, the resin is filtered off and washed with 0.1 M phosphate solution of pH 7.0. Of the 71,550 ATEE units of the soluble subtilisin, 6,250 ATEE/g (8.7%) are bonded to the enzyme resin.

EXAMPLE 6

Preparation of a Maxatase/crosslinked Amberlite XAD-7 resin 10 g of moist Amberlite XAD-7 resin is suspended in 50 ml of water with 20 mM of $CaCl_2$ and 1 g of Maxatase (Maxatase, 500,000 Delft units/g, manufacturer: Gist-Brocades N.V., Holland) is added, whilst stirring. After stirring the mixture at room temperature for 2 hours, the resin is filtered off and the enzyme activity adsorbed is determined. 43.1% of the activity employed are adsorbed onto the resin. The enzyme resin is then crosslinked for 2 hours with a 1.5% strength glutardialdehyde solution and thereafter washed with a total of 500 ml of $H_2O$+20 mM of $CaCl_2$ in portions. 9.6 g of a moist crosslinked enzyme resin to which 36.8% of the activity originally employed was bonded are obtained.

EXAMPLE 7

Preparation of a chymotrypsin/anhydride resin 10 g of an anhydride resin are reacted with 1 g of lyophilised bovine α-chymotrypsin (Merck, Darmstadt/Federal Republic of Germany) according to Example 4. The enzyme has an activity of 105,800 ATEE units/g. 87,210 ATEE units (82.4% of the activity employed can be detected in the filtrate obtained from the enzyme coupling reaction. 5,427 ATEE units/g of enzyme resin (5.1% of the activity employed) remain on the anhydride resin.

EXAMPLE 8

Enzymatic resolution of N-acetyl-DL-phenylglycine methyl ester with a subtilisin/anhydride resin and subsequent acid hydrolysis to give D- and L-phenylglycine 15 g (72.38 mmols) of the N-acetyl-DL-phenylglycine methyl ester prepared according to Example 1 are dissolved in 150 ml of a dioxane/water mixture (25% by volume of dioxane) and 15 g of the subtilisin/anhydride resin prepared according to Example 4 are added, whilst stirring. The pH value is kept constant at pH 7.8 by adding 1 N NaOH with a Methrom titration unit (pH meter E 300 B, Impulsomat E 473 and Dosimat 412, Metrohm, Herisau/Switzerland). After a reaction time of about 19 hours at 25° C., 38.0 ml of 1 N NaOH have been consumed, which corresponds to enzymatic resolution of 52.5% of the N-acetyl-DL-phenylglycine methyl ester employed.

The subtilisin resin is filtered off over a frit and stored at 4° C. until further use. The filtrate is adjusted to pH 9 with solid $Na_2CO_3$ and extracted three times with 200 ml of ethyl acetate and the combined extracts are dried with $Na_2SO_4$. The ethyl acetate is stripped off on a rotary evaporator and the substance which has precipitated is dried over $P_2O_5$ in vacuo. 6.08 g (81.0% of theory) N-acetyl-D-phenylglycine methyl ester of melting point 107° C. are obtained, with an optical rotation of $[\alpha]_{578\ nm}^{25°\ C.} = -174.7°$ (c=1 in ethanol).

Thin layer chromatography on silica gel plates in the solvent system n-butanol/$CH_3COOH/H_2O$=4/1/1 gives a zone which can be stained with iodine but not with ninhydrin and which corresponds to that of the starting material ($R_f$ value=0.61).

The aqueous phase from the first extraction is adjusted to pH 2 with 6 N $H_2SO_4$ and extracted three times with 200 ml of ethyl acetate, the combined extracts are dried with $Na_2SO_4$ and the ethyl acetate is stripped off on a rotary evaporator. The substance which has precipitated is dried over $P_2O_5$ in vacuo. 6.81 g (97.4% of theory) N-acetyl-L-phenylglycine methyl ester of melting point 198° C. are obtained, with an optical rotation of $[\alpha]_{578\ nm}^{25°\ C.} = +154.9°$ (c=1 in ethanol).

Thin layer chromatography under the same conditions as before gives a zone which can be stained with iodine and which corresponds to that of synthetic N-acetyl-phenylglycine ($R_f$ value: 0.48).

3 g each of N-acetyl-D-phenylglycine methyl ester and N-acetyl-L-phenylglycine are dissolved in 30 ml of 2 N HCl and the solution is heated at 80° C. for 4 hours. After cooling the solution, the pH value is adjusted to 6 with 10 N NaOH and the phenylglycine which has precipitated is filtered off and dried over $P_2O_5$ in vacuo.

The yield of D-phenylglycine from N-acetyl-D-phenylglycine methyl ester is 1.99 g (91.3% of theory).

Only one zone, which can be stained with iodine and ninhydrin, can be detected in the thin layer chromatogram. The $R_f$ value of 0.28 to 0.29 is the same as that of synthetic phenylglycine. The optical rotation is:

$[\alpha]_{578\ nm}^{25°\ C.} = -152.3°$ (c=0.6 in 2 N HCl).

The yield of L-phenylglycine from N-acetyl-L-phenylglycine is 2.26 g (96.2% of theory) with a $R_f$ value=0.28, and only one zone which can be stained with iodine and ninhydrin.

$[\alpha]_{578\ nm}^{25°\ C.} = +104.3°$ (c=0.6 in 2 N HCl).

EXAMPLE 9

Enzymatic resoluton of N-acetyl-DL-phenylglycine methyl ester with a chymotrypsin/anhydride resin and subsequent acid hydrolysis to give D- and L-phenylglycine 15 g (72.38 mmols) of the N-acetyl-DL-phenylglycine methyl ester prepared according to Example 1 are resolved with 15 g of a chymotrypsin/anhydride resin, prepared according to Example 6, as described in Example 8. After a reaction time of 17 hours and 20 minutes at 25° C., 37.5 ml of 1 N NaOH are consumed, which corresponds to an enzymatic resolution of 51.8% of the N-acetyl-DL-phenylglycine methyl ester employed.

The enzyme resin and the solutions are worked up as described in Example 7.

Yield of N-acetyl-D-phenylglycine methyl ester of melting point 102° to 106° C.: 7.46 g (99.5% of theory).

$[\alpha]_{578\ nm}^{25°\ C.} = -156.5°$ (c=1 in ethanol).

Only one zone, which can be stained with iodine and has a $R_f$ value of 0.61, can be detected in the thin layer chromatogram.

Yield of N-acetyl-L-phenylglycine of melting point 193° to 196° C.: 6.33 g (90.6% of theory).

$[\alpha]_{578\ nm}^{25°\ C.} = +188.5°$ (c=1 in ethanol).

Only one zone, which can be stained with iodine and has a $R_f$ value of 0.48 to 0.49, can be detected in the thin layer chromatogram.

The acid hydrolysis of 4 g each of N-acetyl-DL-phenylglycine methyl ester and N-acetyl-L-phenylglycine to give D- and L-phenylglycine respectively is effected as indicated in Example 8.

Yield of D-phenylglycine: 2.52 g (86.3% of theory).

$[\alpha]_{578\ nm}^{25°\ C.} = -132°$ (c=0.6 in 2 N HCl).

The zone, in the thin layer chromatogram, which can be stained with ninhydrin and iodine corresponds, with a $R_f$ value of 0.28, to that of synthetic phenylglycine.

Yield of L-phenylglycine: 3.03 g (96.8% of theory).

$[\alpha]_{578\ nm}^{25°\ C.} = +134°$ (c=0.6 in 2 N HCl).

Only one zone, which can be stained with iodine and ninhydrin, and the $R_f$ value 0.28 can be detected in the thin layer chromatogram.

EXAMPLE 10

Enzymatic resolution of N-acetyl-DL-phenylglycine ethyl ester with a subtilisin/anhydride resin and subsequent acid hydrolysis to give D- and L-phenylglycine 10 g (45.19 mmols) of the N-acetyl-DL-phenylglycine ethyl ester prepared according to Example 2 are dissolved in 100 ml of dioxane/water (3:7, by volume), as in Example 8, and 15 g of a subtilisin/anhydride resin (prepared according to Example 5) are added. The mixture is titrated to pH 7.8 with 1 N NaOH as in Example 8. After a reaction time of 16 hours at 25° C., 20.8 ml of 1 N NaOH have been consumed, which corresponds to an enzymatic resolution of 46.0% of the N-acetyl-DL-phenylglycine ethyl ester employed.

Further working up of the mixture was carried out as described in Example 8.

Yield of N-acetyl-D-phenylglycine ethyl ester of melting point 86° C.: 4.83 g (96.6% of theory).

$[\alpha]_{578\ nm}^{25°\ C.} = -151.9°$ (c=1.56% in ethanol).

One zone, which could be stained only with iodine and had a $R_f$ value of 0.59, and which corresponds to the starting material, was found in the thin layer chromatogram.

Yield of N-acetyl-L-phenylglycine of melting point 191° C.: 4.04 g (92.4% of theory).

$[\alpha]_{578\ nm}^{25°\ C.} = +194.7°$ (c=1 in ethanol).

Only one zone, which could be stained with iodine and had a $R_f$ value of 0.49, which also corresponds to the $R_f$ value of synthetic N-acetyl-phenylglycine, could be detected in the thin layer chromatogram.

The enzymatic resolution was repeated 5 times with the same enzyme resin, in each case with new substrate, the same result always being obtained.

The acid hydrolysis of 4 g each of N-acetyl-D-phenylglycine ethyl ester and N-acetyl-L-phenylglycine to give D- and L-phenylglycine respectively was effected as indicated in Example 8.

Yield of D-phenylglycine: 1.96 (71.8% of theory).
$[\alpha]_{578\,nm}^{25°\,C.} = -164.5°$ (c=0.6 in 2 N HCl).
Yield of L-phenylglycine: 2.07 g (75.8% of theory).
$[\alpha]_{578\,nm}^{25°\,C.} = +140.8°$ (c=0.6 in 2 N HCl).
$R_f$ value=0.28.

EXAMPLE 11

Enzymatic resolution of N-acetyl-DL-4-hydroxy-phenylglycine methyl ester with a subtilisin/anhydride resin and subsequent acid hydrolysis to give D- and L-p-hydroxy-phenylglycine 5 g (22.4 mmols) of the N-acetyl-DL-4-hydroxy-phenylglycine methyl ester prepared according to Example 3 are dissolved in 70 ml of dioxane/water (3.7, by volume) and are resolved with 10 g of a subtilisin/anhydride resin as described in Example 8. After a reaction time of 6.5 hours at 25° C., 12.3 ml of 1 N NaOH have been consumed, which corresponds to an enzymatic resolution of 54.9% of the starting material.

The enzyme resin and the solutions are worked up as described in Example 8.

Yield of N-acetyl-D-4-hydroxy-phenylglycine methyl ester of melting point 168° to 170° C: 2.14 g (85.6% of theory).

$[\alpha]_{578\,nm}^{25°\,C.} = -163.2°$ (c=1 in ethanol).

Only one zone, which can be stained with iodine and has a $R_f$ value of 0.62, can be detected in the thin layer chromatogram.

Yield of N-acetyl-L-4-hydroxy-phenylglycine of melting point 194° to 197° C: 1.81 g (77.2% of theory).

$[\alpha]_{578\,nm}^{25°\,C.} = +181.0°$ (c=1 in ethanol).

One zone, which could be stained only with iodine and had a $R_f$ value of 0.50, could be detected in the thin layer chromatogram.

1.5 g each of N-acetyl-D-4-hydroxy-phenylglycine methyl ester and N-acetyl-L-4-hydroxy-phenylglycine were subjected to acid hydrolysis as described in Example 7.

Yield of D-4-hydroxy-phenylglycine from N-acetyl-D-4-hydroxy-phenylglycine: 0.74 g (66.1% of theory).

Only one zone, which can be stained with iodine and ninhydrin and has a $R_f$ value of 0.25, which corresponds to that of synthetic 4-hydroxy-phenylglycine, can be detected in the thin layer chromatogram.

Yield of L-4-hydroxy-phenylglycine from N-acetyl-L-4-hydroxy-phenylglycine: 0.76 g (63.3% of theory).

Only one zone, which can be stained with iodine and ninhydrin and has a $R_f$ value of 0.25 to 0.27, can be detected in the thin layer chromatogram.

What is claimed is:

1. A process for the stereoselective resolution of a DL-phenylglycine derivative which comprises hydrolyzing at 20° to 40° C. and at a pH range of 6 to 8 an ester or amide group on an N-acyl-L-phenylglycine ester or amide in an N-acyl-DL-phenylglycine ester or amide in solution by the action of an enzyme bonded to a carrier to form a mixture of (1)N-acyl-L-phenylglycine and (2)N-acyl-D-phenylglycine ester or amide and separating the N-acyl-D-phenylglycine ester or amide from the N-acyl-L-phenylglycine.

2. A process according to claim 1 in which the enzyme is a proteolytic enzyme.

3. A process according to claim 2 in which the enzyme is a serine protease or sulphydryl-protease.

4. A process according to claim 1, in which the enzyme is subtilisin, α-chymotrypsin, papain, ficin or bromelain.

5. A process of claim 1 wherein the ester or amide group in the N-acyl-D-phenylglycine ester or amide is hydrolyzed under acid conditions.

6. A process according to claim 1 in which the carrier for the enzyme is a copolymer of a methacrylate, methacrylic acid and maleic anhydride, optionally crosslinked by glutardialdehyde.

7. A process according to claim 4, in which the carrier for the enzyme is a copolymer of tetraethylene glycol dimethacrylate, methacrylic acid and maleic anhydride, optionally crosslinked by glutardialdehyde.

8. A process according to claim 4 in which the enzyme is subtilisin (EC 3.4.4.16).

9. A process according to claim 4 in which the enzyme is α-chymotrypsin (EC 3.4.4.5).

10. A process according to claim 4 in which the enzyme is papain (EC 3.4.4.10).

11. A process according to claim 1, in which the DL-phenylglycine derivative corresponds to the formula

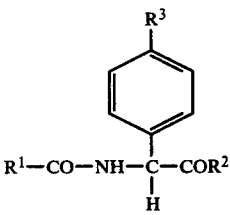

DL-Form in which

R[1] denotes a hydrogen atom or a radical of an optionally substituted aliphatic or araliphatic monocarboxylic or dicarboxylic acid or of a naturally occurring or synthetic α-aminocarboxylic acid, R[2] denotes an alkoxy group, an amino group which is optionally monosubstituted or disubstituted by alkyl, or a radical of a naturally occurring or synthetic α-aminoacid and R[3] denotes a hydrogen atom or a hydroxyl, alkoxy, aralkoxy, aryloxy, cycloalkoxy or acyloxy group.

12. A process according to claim 1, in which the DL-phenylglycine derivative corresponds to the formula

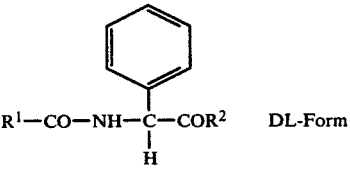

in which

R[1] denotes a hydrogen atom or a mono-, di- or trichloromethyl, trifluoromethyl or w-carboxy-$C_2$-$C_6$-alkyl group and R[2] denotes a methoxy or ethoxy group.

13. A process according to claim 1, in which the DL-phenylglycine derivative corresponds to the formula

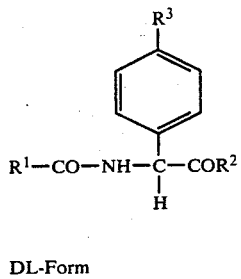

DL-Form in which
R[1] denotes a hydrogen atom or a methyl, mono-, di- or tri-chloromethyl, trifluoromethyl or w-carboxy-$C_2$-$C_6$-alkyl group,
R[2] denotes a methoxy or ethoxy group and
R[3] denotes a hydroxyl, methoxy, ethoxy or acetoxy group.

14. A process according to claim 11, in which R[1] denotes a hydrogen atom or a radical of an aliphatic or araliphatic monocarboxylic or dicarboxylic acid or of a naturally occurring or synthetic α-aminocarboxylic acid and R[3] denotes a hydrogen atom or a hydroxyl group.

* * * * *